(12) United States Patent
Pontius

(10) Patent No.: US 10,932,914 B2
(45) Date of Patent: Mar. 2, 2021

(54) METHOD AND APPARATUS FOR ORTHOPEDIC IMPLANT

(71) Applicant: Uwe R. Pontius, San Antonio, TX (US)

(72) Inventor: Uwe R. Pontius, San Antonio, TX (US)

( * ) Notice: Subject to any disclaimer, the term of this patent is extended or adjusted under 35 U.S.C. 154(b) by 0 days.

(21) Appl. No.: 17/011,783

(22) Filed: Sep. 3, 2020

(65) Prior Publication Data

US 2020/0397588 A1 Dec. 24, 2020

Related U.S. Application Data

(63) Continuation of application No. 16/705,022, filed on Dec. 5, 2019, which is a continuation of application No. PCT/US2019/041518, filed on Jul. 12, 2019.

(60) Provisional application No. 62/697,824, filed on Jul. 13, 2018.

(51) Int. Cl.
*A61F 2/30* (2006.01)
*A61F 2/46* (2006.01)
*A61F 2/28* (2006.01)

(52) U.S. Cl.
CPC ...... *A61F 2/30734* (2013.01); *A61F 2/30749* (2013.01); *A61F 2/4603* (2013.01); *A61F 2002/2892* (2013.01); *A61F 2002/302* (2013.01); *A61F 2002/3023* (2013.01); *A61F 2002/30131* (2013.01); *A61F 2002/30462* (2013.01); *A61F 2002/30593* (2013.01); *A61F 2002/30604* (2013.01); *A61F 2002/30736* (2013.01); *A61F 2310/00017* (2013.01); *A61F 2310/00023* (2013.01); *A61F 2310/00131* (2013.01); *A61F 2310/00161* (2013.01); *A61F 2310/00179* (2013.01)

(58) Field of Classification Search
CPC .......... A61F 2/28; A61F 2/30; A61F 2/30734; A61F 3/30749; A61F 2/389; A61F 2/3868
See application file for complete search history.

(56) References Cited

U.S. PATENT DOCUMENTS

| | | |
|---|---|---|
| 6,203,546 B1 | 3/2001 | MacMahon |
| 7,214,654 B1 | 5/2007 | Schmidt |
| 8,388,690 B2 | 3/2013 | Singhatat et al. |
| 8,414,650 B2 | 4/2013 | Bertele et al. |
| 8,496,662 B2 | 7/2013 | Novak et al. |
| 8,828,087 B2 | 9/2014 | Stone et al. |
| 8,959,741 B2 | 2/2015 | Liu |
| 9,060,873 B2 | 6/2015 | Abdou |
| 9,119,728 B2 | 9/2015 | Wooley |
| 9,211,129 B2 | 12/2015 | Harbison |
| 9,700,414 B2 | 7/2017 | Maxson et al. |
| 9,707,023 B2 | 7/2017 | Ammann et al. |

(Continued)

OTHER PUBLICATIONS

International Search Report issued in corresponding PCT International Patent Application No. PCT/US2019/041518 dated Sep. 6, 2019.

(Continued)

*Primary Examiner* — Jason-Dennis N Stewart
(74) *Attorney, Agent, or Firm* — Pizarro Allen PC

(57) ABSTRACT

A tibial implant may include a plurality of implant subunits. The implant subunits may be configured for individual insertion within a wedge-shaped-void of the tibia. The implant subunits may further be configured for assembly in order to provide an implant substantially covering an exposed portion of cortical bone formed when performing a surgical osteotomy. Methods and kits for insertion and assembly of implants are further described.

5 Claims, 12 Drawing Sheets

(56) References Cited

U.S. PATENT DOCUMENTS

| | | |
|---|---|---|
| 2003/0105526 A1 | 6/2003 | Bryant et al. |
| 2008/0125865 A1 | 5/2008 | Abdelgany et al. |
| 2010/0016858 A1 | 1/2010 | Michel |
| 2012/0095506 A1 | 4/2012 | Mayer et al. |
| 2013/0190815 A1 | 7/2013 | Mansmann |
| 2014/0358246 A1 | 12/2014 | Levy et al. |
| 2015/0335367 A1 | 11/2015 | Austin et al. |
| 2016/0128748 A1 | 5/2016 | Tepic et al. |

OTHER PUBLICATIONS

Written Opinion issued in corresponding PCT International Patent Application No. PCT/US2019/041518 dated Sep. 6, 2019.

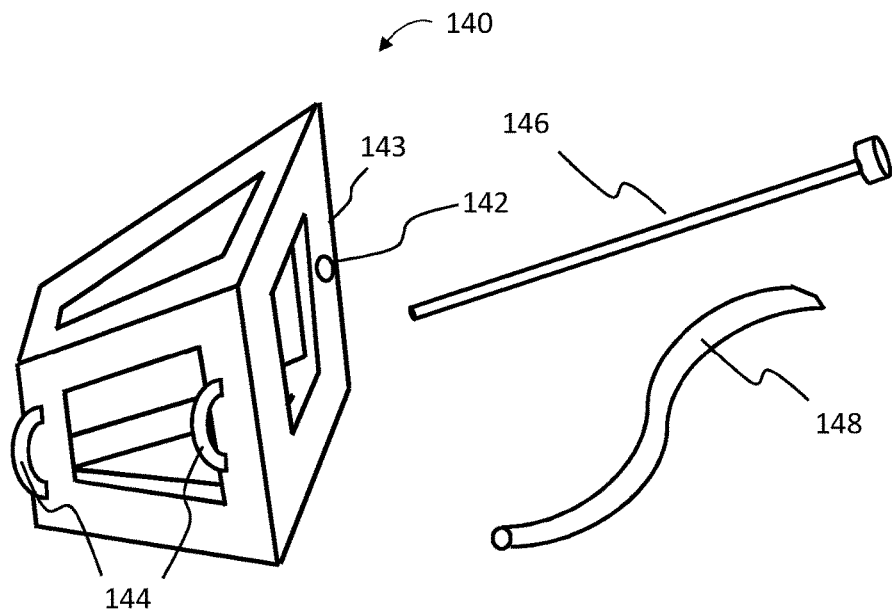
Fig. 18
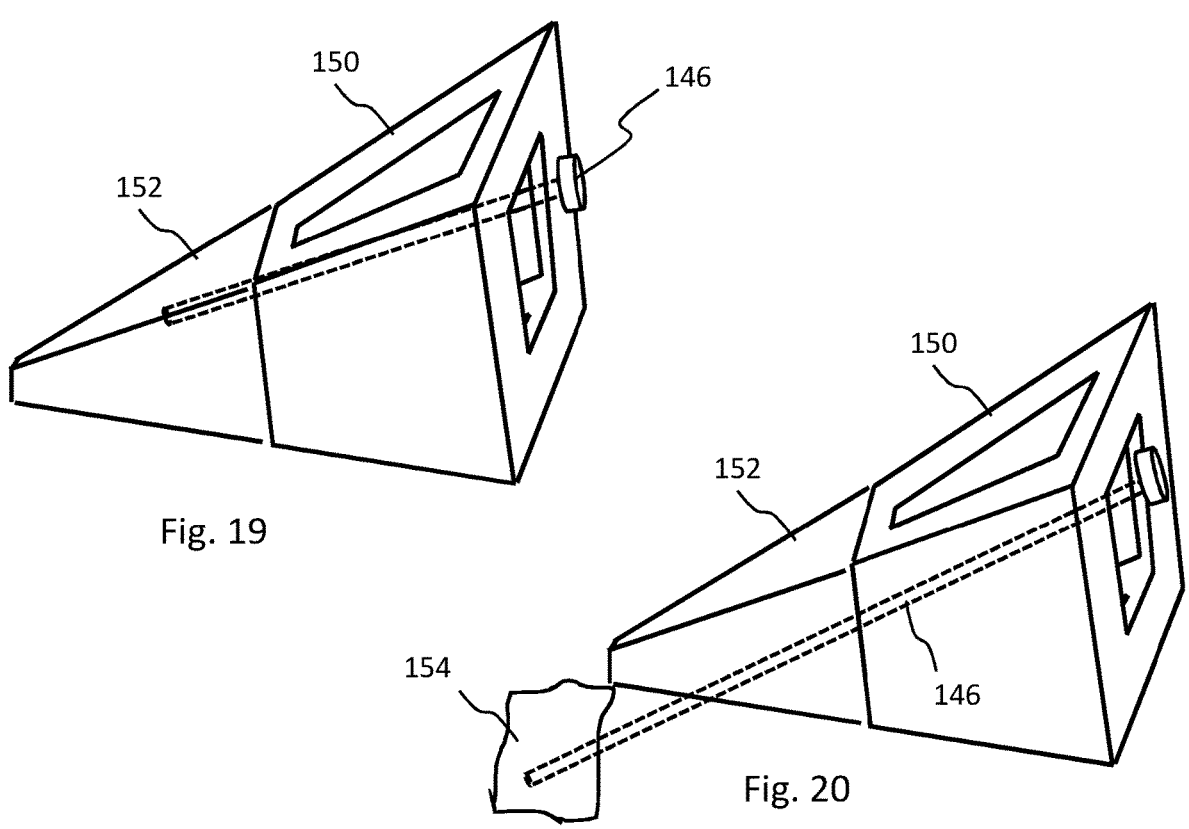
Fig. 19
Fig. 20

METHOD AND APPARATUS FOR ORTHOPEDIC IMPLANT

CROSS-REFERENCE TO RELATED APPLICATIONS

This application is a continuation of U.S. application Ser. No. 16/705,022, filed Dec. 5, 2019, which is a continuation of PCT International Patent Application No. PCT/US2019/041518 filed Jul. 12, 2019, titled "Method and Apparatus for Orthopedic Implant," which claims priority to U.S. Provisional Patent Application No. 62/697,824 filed Jul. 13, 2018, also titled "Method and Apparatus for Orthopedic Implant." The full disclosure of each of the aforementioned patent applications is herein fully incorporated by reference.

FIELD

This application relates to methods, apparatuses, and kits for performing tibial osteotomies and repairs of the knee.

BACKGROUND

Generally, osteotomies of the knee are designed to adjust the geometry of the knee, thereby rebalancing articular forces on the knee joint due to the patient's arthritic disease. For example, forces may be redistributed from one side of the knee joint to another in order to alleviate pain caused by knee degeneration with resultant structural abnormalities. In order to accomplish these objectives, a transverse cut is made in the tibia, and either distraction with interposition grafting or removing a wedge of bone is performed. Thus, the alignment of the tibia with respect to the femur and knee joint may be adjusted. The bone may then be secured in this position. For example, bone may be secured in place by screwing metal plates to the bones and/or by inserting one or more sections of structural material, such as a graft of hard bone taken from an iliac crest. In such procedures, only a portion of the wedge-like-cut-out may be filled with hard bone. For example, hard bone may be positioned adjacent a medial side of the wedge-like-cut-out and partially inserted therein such that it may be in contact with only a limited section of cortical bone in the wedge-like-cut-out of the patient's tibia. However, a significant amount of the wedge-like-cut-out may remain unsupported or insufficiently supported with structural material generally designed to maintain the separation of bony surfaces and to encourage bone growth. Present designs in use are insufficient for supporting loads associated with patients with morbid obesity (BMI>40). Accordingly, the patient may be left with only insufficient structural support during healing causing the operation to fail.

While osteotomies have proven to be valuable in providing relief for certain patients suffering from joint degeneration and other joint abnormalities of the knee, the procedure may be challenging for both the patient and surgeon. Notably, the surgeon may find it difficult to properly execute an osteotomy without substantially damaging the surrounding tissues adjacent the tibia and knee. In addition, only limited structural support may be provided by the structural material. Some patients, such as obese patients, may find it particularly difficult to successfully recover from a tibial osteotomy. Accordingly, patient recovery may tend to be slow, difficult, and painful.

Accordingly, there is a need for surgical methods and related implants and surgical kits designed for effective insertion of implants within the tibia and/or positioning of the implants therein while minimizing associated tissue damage for the patient. There is further a need for methods that provide improved mechanical support in the cut-out sections of the tibia, speeding recovery for patients and minimizing structural failures. There is further a need for methods for treating knee degeneration and/or correcting abnormalities in the knee that may be applicable for use in patients, such as obese patients, who may be ineligible for other types of surgical intervention, and who may be at increased risk of post-surgical complications and incomplete recovery from surgery, especially following total knee replacement.

SUMMARY

In some embodiments, generally U-shaped portions of an implant for insertion into a wedge-shaped void of a patient's tibia are described. The U-shaped portion of an implant may include a plurality of implant subunits, the plurality of implant subunits configured to form a generally U-shaped portion of an implant when the plurality of implant subunits are combined. The plurality of implant subunits may further be configured for individual insertion into a surgical opening adjacent a wedge-shaped void in a patient's tibia. The U-shaped portion of an implant may be configured to overlap a substantial area of an exposed region of cortical bone created when forming said wedge-shaped void. For example, the U-shaped portion of an implant may cover an area that is greater than about 75% of the area of the exposed region of cortical bone. The implant may further include one or more cables attached to at least a group of implant subunits among the plurality of implant subunits, the one or more cables configured such that when the one or more cables are tightened, the group of implant subunits may be automatically positioned to form the U-shaped portion of an implant.

In some embodiments, a surgical opening for insertion of implant subunits may be significantly reduced as compared to a minimum sized opening sized for insertion of an implant suitable for substantially filling said wedge-shaped void. Moreover, the individual subunits may be readily positioned around the rim of hard cortical bone adjacent the wedge-shaped void. For example, a system of one or more cables may be designed to automatically position implant subunits in a desired configuration. Thus, in some embodiments, a surgeon may both insert the implant subunits using incisions sized to minimize trauma and assemble an implant quickly and without extensive manual manipulation of implant sub-unit once generally positioned within the wedge-shaped void, such as may otherwise be required if a surgeon were manually positioning each subunit individually to a final position or if the surgeon were inserting a pre-formed implant already sized to cover an exposed rim of cortical bone.

In some embodiments, an implant may further be constructed to withstand loads associated with patients who may be obese or morbidly obese. For example, in some embodiments, an implant may be assembled from a plurality of implant subunits, the implant subunits configured to cover a substantial area of an exposed region of cortical bone. In some embodiments, implant subunits may further be made of carbon-fiber or carbon-fiber reinforced PEEK. In some embodiments, implant subunits may comprise a carbon-fiber scaffold, including, for example, an internally formed scaffold, an externally formed scaffold, or a combination of both. Thus, implants herein may be configured for both reduced damage during insertion and/or positioning, and the implants may be configured to provide immediate and improved support during healing. In some embodiments, obese patients, including patients who weigh up to about 300 pounds to about 500 pounds may be surgically treated using implants and methods described herein. In some embodiments, implants and methods herein may be used to surgically treat patients without substantially compromising adjacent regions of tissue which can complicate other surgical procedures which a patient may be eligible for in the future, such as total knee replacement.

In some embodiments, kits for performing a surgical repair of the tibia are described herein. The kits may include a plurality of implant subunits; wherein the plurality of implant subunits are configured for individual insertion into a wedge-shaped void of tibial bone; wherein the plurality of implant subunits are further configured for arrangement with respect to one another in order to form a generally U-shaped portion of an implant, the U-shaped portion configured to substantially cover an exposed rim of cortical bone on the periphery of the cross-section. The kits may further include one or more linking members; and instructions for how to assemble said plurality of implant subunits into said implant using the one or more linking members.

In some embodiments, kits for performing a surgical repair of the tibia are described herein. The kits may include a plurality of implant subunits; wherein the plurality of implant subunits are configured for individual insertion of implant subunits into a wedge-shaped void of tibial bone; wherein the plurality of implant subunits are further configured for arrangement with respect to one another in order to form an implant shaped to substantially cover an exposed rim of cortical bone defined by the wedge-shaped void. The kits may further include one or more linking members; and instructions for how to connect the plurality of implant subunits to the one or more linking members and how to automatically position the implant subunits in order to form the implant when tightening the one or more linking members; wherein the plurality of implant subunits include a plurality of implant subunits configured for bearing a patient's weight, the plurality of implant subunits comprising a substantially hollow carbon-cage.

In some embodiments, methods for performing a surgical repair of the tibia are described herein. The methods may include creating an opening in a patient's tissue in order to expose a portion of the patient's tibia; cutting a portion of the patient's tibia to create a wedge-shaped void in the patient's tibia; individually inserting each of a plurality of implant subunits through the opening in the patient's tissue; and positioning the implant subunits within the wedge-shaped void in order to form a generally U-shaped portion of an implant.

BRIEF DESCRIPTION OF THE DRAWINGS

FIG. 18 is a side perspective view of an implant subunit and apparatus for linking the implant subunit to another implant subunit and/or to a portion of a patient's bone.

FIG. 19 is a side perspective view of two implant subunits linked together using a pin.

FIG. 20 is a side perspective view of two implant subunits linked together using a pin and further attached to a portion of a patient's bone.

DETAILED DESCRIPTION

The following terms as used herein should be understood to have the indicated meanings.

When an item is introduced by "a" or "an," it should be understood to mean one or more of that item.

"Comprises" means includes but is not limited to.

"Comprising" means including but not limited to.

"Having" means including but not limited to.

Where a range of values is described, it should be understood that intervening values, unless the context clearly dictates otherwise, between the upper and lower limits of that range, and any other stated or intervening value in other stated ranges, may be used within embodiments described herein.

The methods, kits, and apparatuses described herein are generally related to surgical techniques for performing tibial osteotomies and inserting implants into the voids created by the osteotomies. The methods, kits, and apparatuses described herein may be used for treating knee joint degenerative conditions and/or other abnormalities. In some embodiments, the methods, kits, and apparatuses described herein may be specifically designed for patients (e.g., morbidly obese patients) who may have decreased eligibility for other types of surgical intervention, such as total or partial knee replacement, and/or who may be at increased risk of post-surgical complications and compromised recovery from surgery with previously existing methods.

Figure 1:
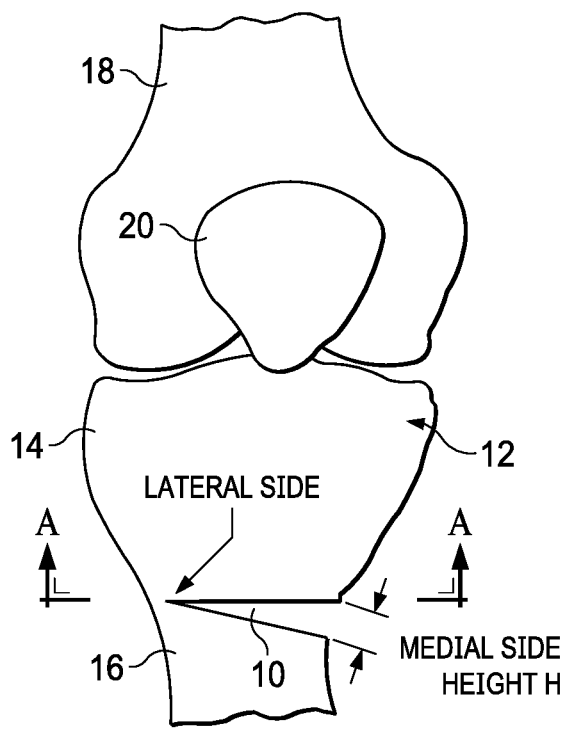
FIG. 1 is an anterior view of a right knee joint and surrounding anatomy showing a wedge-like-section removed from a patient's tibia.

During a tibial osteotomy, one or more incisions may be made below the patient's knee joint in order to create an opening exposing the patient's tibia. The one or more incisions may be sufficient in size to create an opening in the patient's tissue suitable to access tibial bone and to allow a surgeon to cut into the patient's tibia and form a wedge-like void section therein, sometimes referred to herein as a wedge-shaped void. For example, FIG. 1 shows an anterior view of a knee joint and associated anatomical structures. As shown therein, a wedge-shaped void 10 may be made in the tibia 12. For example, a transverse cut may be made in the tibia and a force may be applied to separate the exposed surfaces. In some embodiments, wedge-shaped void 10 may be formed slightly below an upper portion 14 of the tibia and within a lower portion 16 of the tibia. The wedge-shaped void 10 may include a medial side generally defining a wedge height H and a lateral side which may be tapered. Additional anatomical structures associated with the knee joint and shown in FIG. 1 include the femur 18 and patella (knee cap) 20. The fibula is not shown for clarity.

Figure 2:
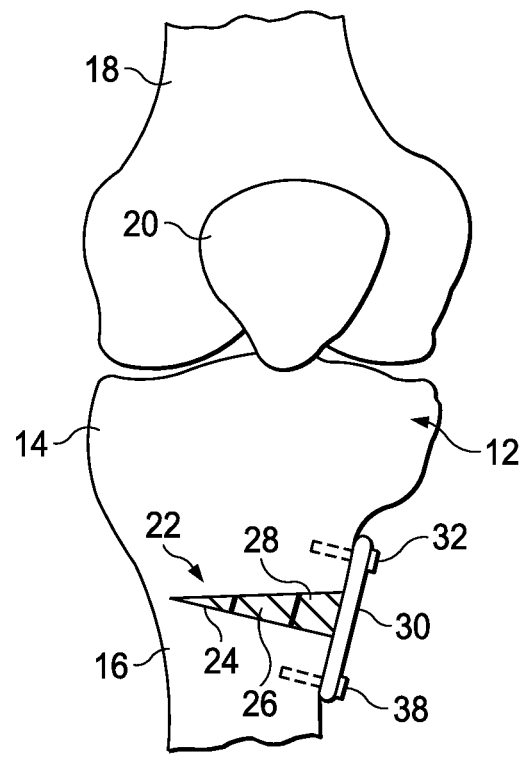
FIG. 2 is an anterior view of the knee joint shown in FIG. 1 with a generally U-shaped implant inserted within the patient's tibia and stabilized medially with a metal fixation plate.

Formation of wedge-shaped void 10 may allow a surgeon to adjust the patient's anatomy so that abnormal forces related to the patient's disease progression are changed in the direction of equalizing medial and lateral tibial joint forces. Following this adjustment, as shown in FIG. 2, an implant (such as exemplary generally U-shaped implant 22 or another implant described herein) may be positioned within wedge-shaped void 10 so that the adjusted or preferred anatomy is substantially maintained during healing. In some embodiments, implants herein may be generally U-shaped implants (such as may include a curved generally U-shaped implant, shaped so that the implant may generally follow a contour of a section of cortical bone exposed when making a wedge-shaped void), ring-shaped, or other suitable shape. In the embodiment shown in FIG. 2, the generally U-shaped implant 22 may be made from a plurality of implant subunits, including, for example, the implant subunits 24, 26, and 28, discussed in further detail herein in relation to FIG. 6, for example. Once generally U-shaped implant 22 is positioned in wedge-shaped void 10, a metal retaining plate 30 may be secured to tibia 12 across the gap with screws 32, 38 for example, to help keep the gap from opening up and keep the implant 22 in place.

Figure 3:
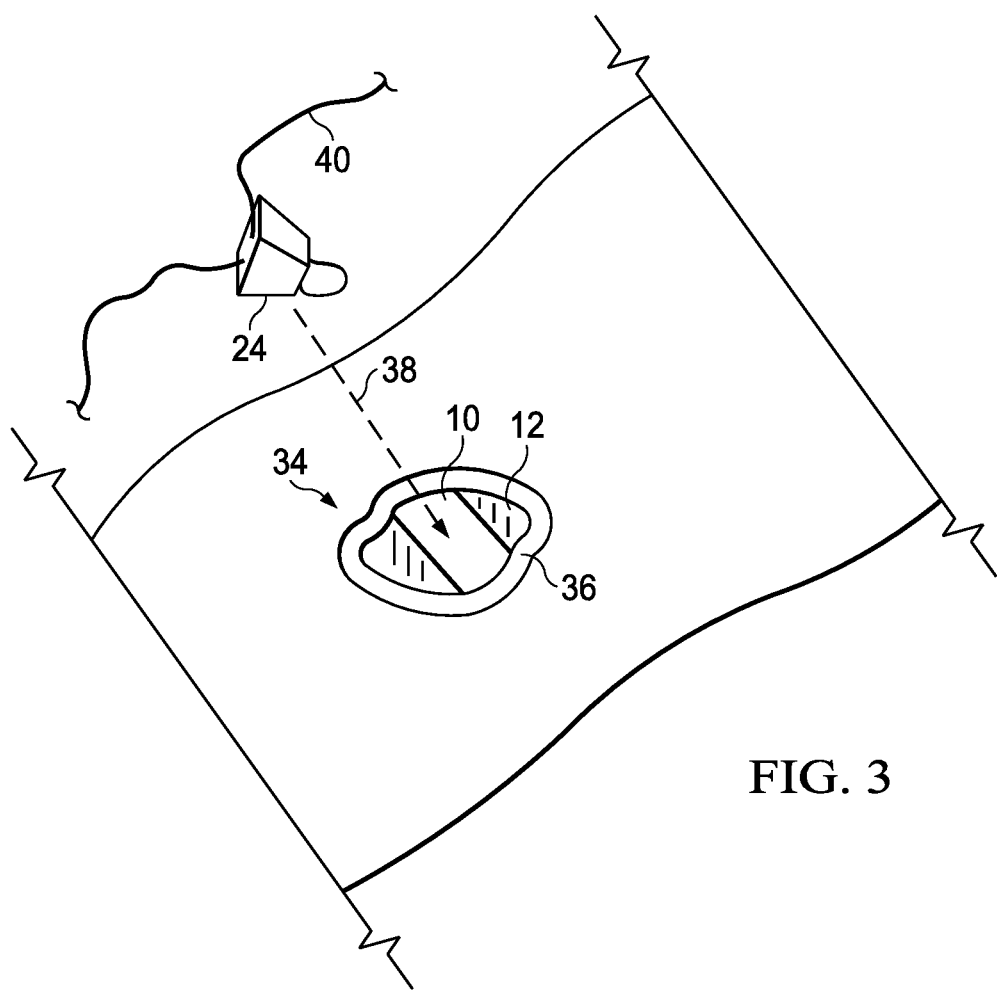
FIG. 3 is a medial perspective view of a patient's knee during part of a surgical osteotomy and repair procedure.

FIG. 3 shows a patient's knee during a part of a surgical osteotomy and repair procedure. As shown therein, a surgeon may create a surgical opening 34 through the skin and other soft tissue in a region near a patient's knee in order to expose a portion of the patient's tibia 12. A surgeon may further create a wedge-shaped void 10 in the tibia. For example, a surgeon may make a cut in the tibia 12 and apply a force to separate the bone in order to create wedge-shaped void 10. In some embodiments, surgical saws, files and/or wedges may be shaped, sized and/or otherwise suitably configured to facilitate creation of a wedge-shaped void 10 using an opening 34 of reduced dimension compared to the size of an implant to be inserted into the void 10. Accordingly, damage to patient tissues, including, for example, tissue 36 near or adjacent the opening 34, may be reduced or minimized while creating the wedge-shaped void 10. As described below, some embodiments of methods herein may further be designed to minimize damage to patient's tissues in other steps in performing an osteotomy, such as when inserting, positioning, and/or securing implant subunits together, or any combinations of the aforementioned steps.

For example, in some embodiments of methods herein, a surgeon may individually insert a plurality of implant subunits, such as exemplary implant subunit 24 (insertion of which is indicated by dashed arrow 38), to fully or in-part fill in wedge-shaped void 10. The implant subunits may be substantially reduced in size as compared to the overall size of a corresponding implant assembled therefrom. For example, in some embodiments, implant subunits described herein may individually subtend an area that is reduced by about 10% to about 70% as compared to an area subtended by an implant made from the implant subunits collectively if such an implant were inserted as a whole. Accordingly, in some embodiments, a surgeon may be able to insert the plurality of implant subunits within wedge-shaped void 10 using an opening 34 of reduced size.

An implant may then be made or assembled by positioning the inserted plurality of implant subunits in order to form the implant. In some embodiments, an implant may be assembled from implant subunits, wherein the implant subunits are configured to support a weight of an obese or a morbidly obese patient when the implant subunits are positioned and secured together within a wedge-shaped void 10. To facilitate support, a group of implant subunits may be configured for positioning adjacent to and substantially covering an exposed area of hard cortical bone within the wedge-shaped void 10. In addition, implant subunits may be constructed and formed of a material suitable to withstand forces needed to support an obese or morbidly obese patient. For example, in some embodiments, implant subunits may be made from or may include a carbon-fiber. In some embodiments, a carbon-fiber may be used together with one or more other biocompatible materials to form a carbon-fiber composite. In some embodiments, an implant subunit may comprise a carbon-fiber scaffold, including, for example, an internally formed scaffold, an externally formed scaffold, or a combination thereof. Thus, implants herein may be configured for both reduced damage during insertion and/or positioning of implant subunits, and the implants may be configured to provide immediate and improved support during healing.

In some embodiments, at least some of the positioned implant subunits may further be linked together to increase the stability of an implant. For example, as shown in FIG. 3, exemplary implant subunit 24 may include one or more cables 40. As described further in relation to FIG. 6 and FIG. 7, the one or more cables 40 may be linked or attached to different implant subunits and tightened in order to link the implant subunits together. In some embodiments, as a surgeon inserts individual implant subunits, the one or more cables 40 may be tightened as necessary to help position or link implant subunits together. In some embodiments, a surgeon may insert a group of implant subunits and then use one or more cables to tighten the inserted implant subunits together, thereby forming a secured implant or part of an implant. Insertion and positioning of implant subunits may also be accomplished in stages. For example, at least some of a group of implant subunits may be inserted and positioned in order to create a part of an implant. Additional implant subunits may then be inserted and positioned in one or more additional stages, such as further described below in relation to FIG. 6.

Figure 4:
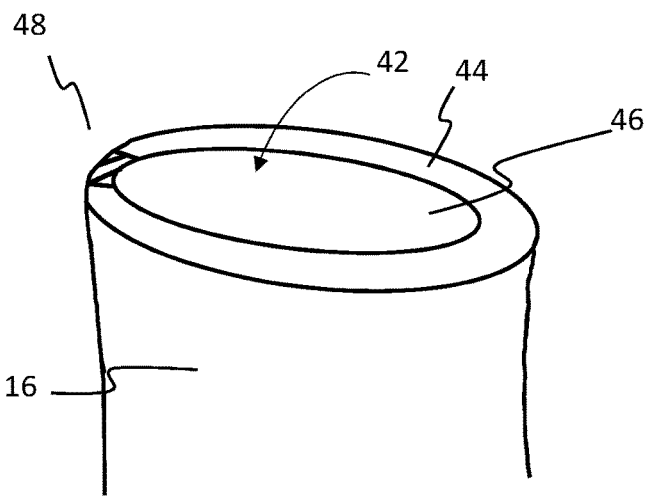
FIG. 4 is a perspective cross-section view of the lower portion of the tibia taken in the direction of arrow A-A indicated in FIG. 1 showing an exposed upper surface of the tibia formed by making a wedge-shaped void therein and a remaining hinge portion of the tibia.
Figure 5:
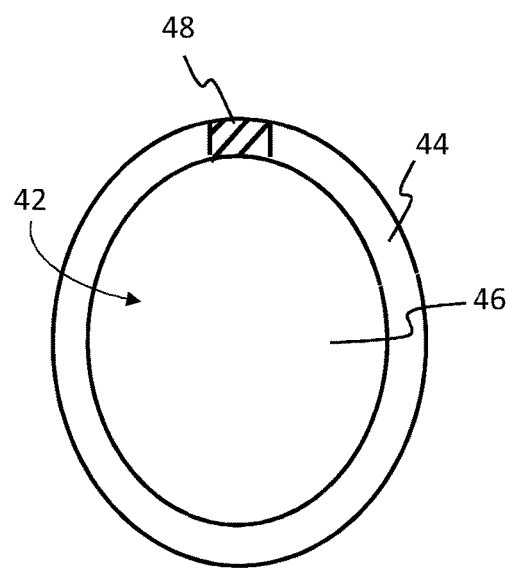
FIG. 5 is a top plan view of the cross-section of the tibia shown in FIG. 4.

FIG. 4 is a perspective cross-sectional view of the lower portion 16 of the tibia taken in the direction of arrow A-A indicated in FIG. 1. As shown therein, formation of wedge-shaped void 10 may expose an upper surface 42 of the tibial bone. The exposed upper surface 42 may include a rim 44 of hard cortical bone and an interior portion 46 of exposed trabecular bone, the interior portion 46 of exposed trabecular bone being considerably weaker than the cortical bone of rim 44. Internal structures of the interior portion 46 of exposed trabecular bone are not shown for clarity. A hinge portion 48 of tibial bone, which may or may not be present, is also shown in FIG. 4. If present, the thickness of hinge portion 48 may depend, for example, upon where an implant is positioned, properties of the bone, and the amount of correction required in surgery. FIG. 5 is a plan view of the lower portion 16 of the tibia taken in the direction of arrow A-A indicated in FIG. 1 showing the exposed upper surface 42 and the remaining hinge portion 48 of tibial bone.

Figure 6:
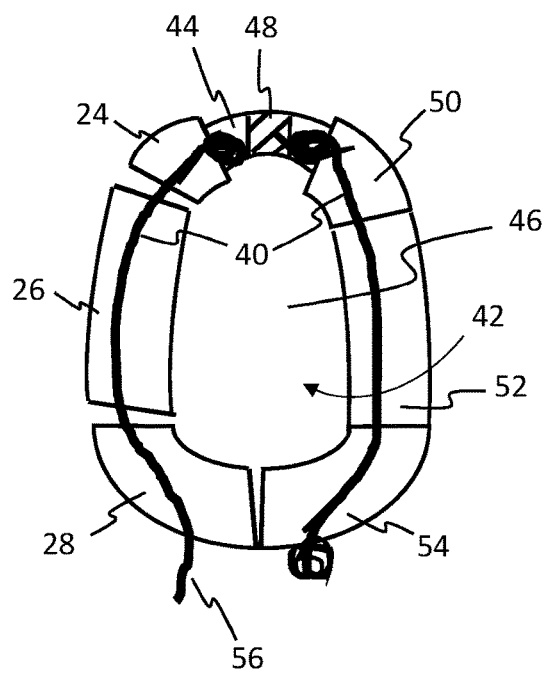
FIG. 6 shows the exposed upper surface of the tibia and hinge portion of remaining bone (as shown in FIG. 5) together with implant subunits and a first embodiment of one or more cables.

In some embodiments, insertion and positioning of implant subunits may be accomplished in one or more stages. For example, FIG. 6 shows the exposed upper surface 42 and remaining hinge portion 48 (also shown in FIGS. 4 and 5) together with implant subunits (24, 26, 28, 50, 52, and 54) partially positioned during an intermediate stage in making a generally curved U-shaped implant 22. For example, implant subunits (24, 26, 28, 50, 52, and 54) may be inserted through opening 34 and generally positioned on the upper surface 42 of the exposed tibia. The subunits 50, 52, and 54 may be generally positioned and one or more cables 40 (e.g., one or more cables internally threaded within subunits therein) may be engaged or pulled to assist in securing the implant subunits (50, 52, and 54) together. In some embodiments, the one or more cables may be attached internally or externally to one or more of the subunits (24, 26, 28, 50, 52, and 54) using one or more fasteners, holes, hooks, or combinations thereof. For example, the one or more cables 40 may be attached so that when the one or more cables 40 are tightened, forces are directed on the implant subunits (50, 52, and 54) to automatically pull the subunits in order to achieve a desired alignment, such as a curled alignment following a part of generally U-type shape. In some embodiments, adjacent faces of the implant subunits (50, 52, and 54) may be angled or shaped to encourage correct relative positioning of the implant subunits (50, 52, and 54) and/or to minimize risk that any implant subunits may buckle or twist inappropriately. Additional subunits 24, 26, and 28 may then be generally positioned and the one or more cables 40 further tightened to help align and/or secure the subunits 24, 26, and 28. For example, to tighten the one or more cables 40, one or more free ends 56 of the one or more cables 40 may be pulled suitably taut to help align and/or secure additional subunits 24, 26, and 28 together with the implant subunits 50, 52, and 54. The suitably taut cable may then be crimped in order to form generally U-shaped implant 22.

In some embodiments, all of the implant subunits (24, 26, 28, 50, 52, and 54) of generally U-shaped implant 22 may be generally positioned on the upper surface 42. One or more cables 40 may further be attached to the implant subunits (24, 26, 28, 50, 52, and 54). For example, the one or more cables 40 may be attached to the implant subunits (24, 26, 28, 50, 52, and 54) during insertion and/or positioning. Alternatively, the one or more cables may be attached to all or some group of the implant subunits (24, 26, 28, 50, 52, and 54) prior to insertion. For example, the one or more cables 40 may be internally threaded, hooked, or both to the implant subunits (24, 26, 28, 50, 52, and 54). Once all of the subunits are inserted and generally positioned on the upper surface 42, a surgeon may engage one or more free ends 56 of the one or more cables 40. The implant subunits (24, 26, 28, 50, 52, and 54) may be attached to the one or more cables 40 such that when a surgeon pulls on the free ends 56 of the one or more cables 40 adjacent subunits may be directed together so as to automatically achieve a desired shape, such as a generally U-type shape. In some embodiments, adjacent faces of the implant subunits (24, 26, 28, 50, 52, and 54) may be angled or shaped to encourage correct relative positioning of the implant subunits (24, 26, 28, 50, 52, and 54) and/or to minimize risk that any implant subunits may buckle or twist in an inappropriate manner.

In other embodiments, one or more cables 40 may be threaded or otherwise attached to subunits of a generally U-shaped implant 22 in other suitable ways. In addition, the one or more cables 40 may further be secured or crimped in one or more alternative or additional positions to help secure subunits in order to stabilize a generally U-shaped implant 22.

Figure 7:
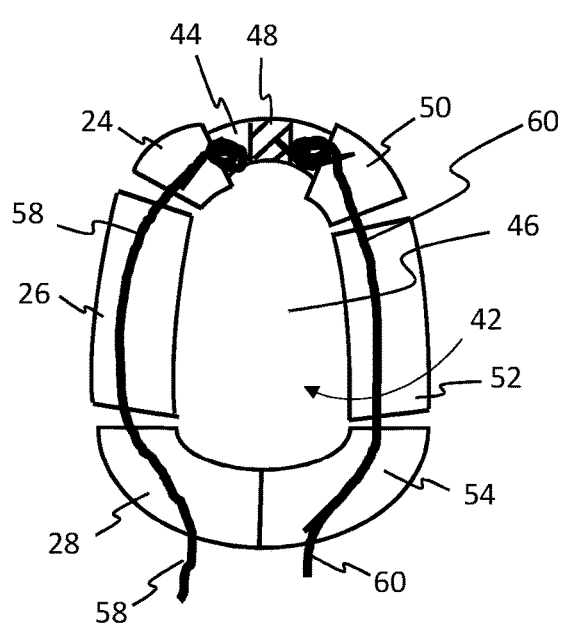
FIG. 7 shows the exposed upper surface of the tibia and hinge portion of remaining bone (as shown in FIG. 5) together with implant subunits and a second embodiment of one or more cables.

For example, FIG. 7 shows the top of exposed upper surface 42 together with implant subunits (24, 26, 28, 50, 52, and 54) in another embodiment for linking the subunits of a generally U-shaped implant 22. In the embodiment shown in FIG. 7, two separate groups of one or more cables are used to stabilize generally U-shaped implant 22. For example, a first group of one or more cables 58 may be threaded through each of the subunits 24, 26, and 28. A second group of one or more cables 60 may be threaded through each of the subunits 50, 52, and 54. Following general positioning of subunits, the first cable group 58 and second cable group 60 may be pulled, separately or together, to help position and/or stabilize the subunits (24, 26, 28, 50, 52, and 54) in order to form generally U-shaped implant 22.

More generally, in some embodiments herein, one or more cables may be used to secure one or more implant subunits that may be positioned laterally with respect to one or more medially positioned implant subunits. For example, one or more laterally positioned subunits may be positioned or secured together first. After positioning and/or securing the laterally positioned implant subunits in place, one or more medially positioned implant subunits may then be positioned or secured in place, such as by forcing the one or more medially positioned implant subunits together with the one or more medially positioned implant subunits by pulling on free ends of one or more cables. A remaining section of cable may then be crimped and cut to a desired length if necessary. Advantageously, in some of those embodiments, a surgeon may have ready access to free ends of cables because the free ends may be positioned near the medial end of wedge-shaped void 10, a position which is near the opening 34 where manipulation of cables may be more easily accomplished. Some of those embodiments may, therefore, simplify the surgery, reduce time, and minimize risk of damage to patient tissues while positioning and/or securing implant subunits together.

Figure 8:
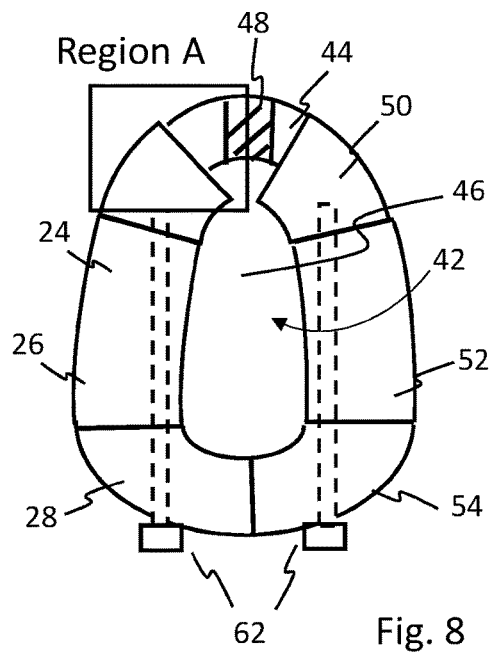
FIG. 8 shows the exposed upper surface of the tibia and hinge portion shown in FIG. 5 together with an embodiment of implant subunits and pins or screws for securing the implant subunits together.

FIG. 8 shows another embodiment for securing generally U-shaped implant 22. As shown in FIG. 8, a generally U-shaped implant 22 may be secured using one or more pins or screws 62. Pins or screws 62 may, for example, extend through one or more subunits of generally U-shaped implant 22. In some embodiments, the one or more pins or screws 62 may further extend through one or more sections of adjacent bone (as also shown in FIG. 20).

Figure 9:
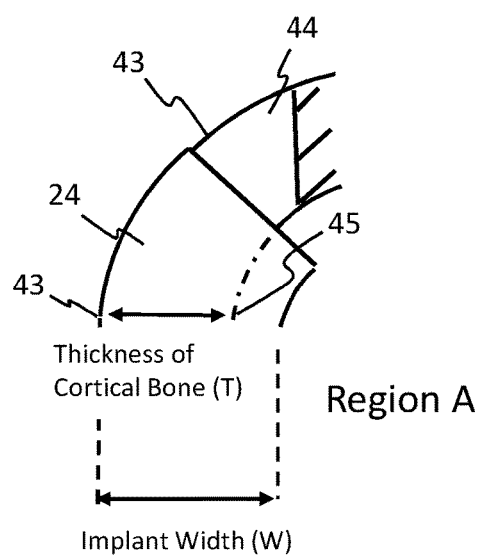
FIG. 9 is an enlarged view of the Region A in FIG. 8 indicating an implant width and thickness of cortical bone in a rim portion of an exposed surface of the tibia.

As shown in each of FIGS. 6-8, a generally U-shaped implant 22 may be configured to overlap with a substantial area of exposed rim 44 of hard cortical bone. Thus, in contrast to other implants, such as implants involving use of autografts, where a significant amount of rim 44 may remain unsupported by hard material or only insufficiently supported with matrix material, generally U-shaped implant 22 (and other implants herein) may be configured to engage hard cortical bone substantially throughout wedge-shaped void 10. For example, in some embodiments, a plurality of implant subunits (e.g., a plurality of subunits of exemplary U-shaped implant 22 or other implants herein) may be inserted within a wedge-shaped void 10 and positioned over rim 44 to cover greater than about 50%, greater than about 75%, greater than about 95%, or up to about 100% of the exposed area of rim 44. Referring to FIG. 9, which is an enlarged view of Region A in FIG. 8, in some embodiments, generally U-shaped implant 22 may be characterized by an implant width (W). In FIG. 9, to better show the overlap of implant subunit 24 and rim 44, a portion of the interior boundary of rim 44 underneath implant subunit 24 is shown as dot-dash line 45. The outer boundary 43 of rim 44 may substantially overlap with the outer boundary of implant subunit 24. In some embodiments, the implant width W may be at least as wide as the thickness (T) of cortical bone. For example, in some embodiments, an implant width may range from about 1.2 times to about 2.5 times the thickness of cortical bone (T). The implant subunits 24, 26, 28, 50, 52, and 54 of U-shaped implant 22 may be constructed, secured, and positioned over a substantial area of the exposed rim 44 to increase support and strengthen generally U-shaped implant 22 so that it may support a weight of an obese or morbidly obese patient. Furthermore, significant support may be present during times immediately following surgery.

In some embodiments, areas of wedge-shaped void 10 that are not filled by a generally U-shaped implant 22 may be filled with one or more filling materials, which may be osteointegrative materials, for example. For example, regions of wedge-shaped void 10 that are not occupied by generally U-shaped implants 22 may be filled with one or more filling materials suitable to provide additional structural support, including support suitable for minimizing risk of displacement of implant subunits. The one or more filling materials may further be configured to promote processes including osteogenesis, osteoinduction, osteoconduction, minimize risk of infection, and any combination thereof. For example, in some embodiments, portions of wedge-shaped void 10 not filled by U-shaped implant 22 may be filled with demineralized bone matrix, hydroxyapatite, one or more growth factors, other suitable matrix materials, and any combination thereof.

In some embodiments, areas of wedge-shaped void 10 that are not filled by generally U-shaped components or portions of an implant may be filled by one or more secondary implant subunits, such as some of the implant subunits described herein with respect to generally U-shaped implants (22, 76). And, in some embodiments, generally U-shaped implants (22, 76) described herein may function as generally U-shaped portions of an implant, which may or may not include one or more secondary implant subunits. Secondary implant subunits, which may be configured for positioning adjacent interior portion 46 of exposed upper surface 42, may generally not experience the same stresses as implant subunits positioned adjacent rim 44. Accordingly, in some embodiments, secondary implant subunits may be configured differently than implant subunits positioned adjacent rim 44. In some embodiments, secondary implants may serve a role in minimizing risk of displacement of implant subunits positioned adjacent rim 44. In some embodiments, one or more secondary implant subunits may help guide positioning of implant subunits positioned adjacent rim 44.

For example, one or more secondary implant subunits may be placed over interior portions 46 of exposed upper surface 42. Implant subunits may then be positioned around the one or more secondary implant subunits, and tightening of cables may force the implant subunits to adopt a proper position around the secondary implant subunits. In some embodiments, secondary implant subunits may be made from one or more highly porous materials and may be configured to promote osteogenesis, for example.

Figure 10:
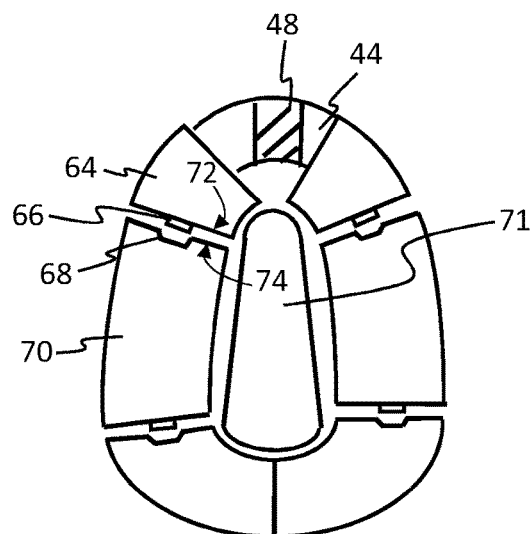
FIG. 10 shows a top plan view of implant subunits in an embodiment for assembling an implant.

In some embodiments, two or more implant subunits among a plurality of implant subunits may be sized for insertion and configured for effective positioning when forming an implant. For example, two or more implant subunits may be inserted and generally positioned within wedge-shaped void 10. Further positioning of the two or more implant subunits may then be achieved when a surgeon directs the two or more implant subunits together. For example, in some embodiments, a surgeon may direct two or more implant subunits together when tightening one or more cables. In some embodiments, correct alignment of the two or more implant subunits for proper positioning during implant assembly may be encouraged because the two or more implant subunits may possess a complementary shape. For example, as shown in FIG. 10, a first implant subunit 64 may include one or more surface features 66 that may be complementary in shape with one or more surface features 68 present on another surface of an adjacent or second implant subunit 70. For example, complementary features 66, 68 of the surfaces 72, 74 may help guide the surfaces 72, 74 to abut together in a correct orientation when a surgeon directs the surfaces to contact each other. For example, a surgeon may direct the surfaces 72, 74 to contact each other by pulling on one or more cables and/or inserting one or more screws or pins (not shown). By way of nonlimiting example, complementary features herein may include grooves, slots, ridges, other suitable shapes, and any combinations thereof. In some embodiments, positioning and securing of implant subunits may be achieved at about the same time or in a single step when a surgeon engages one or more cables and/or inserts one or more screws or pins in order to force adjacent subunits together. In some embodiments, one or more complementary features may be included on one or more secondary implant subunits such as secondary implant subunit 71 shown in FIG. 10.

Figure 11:
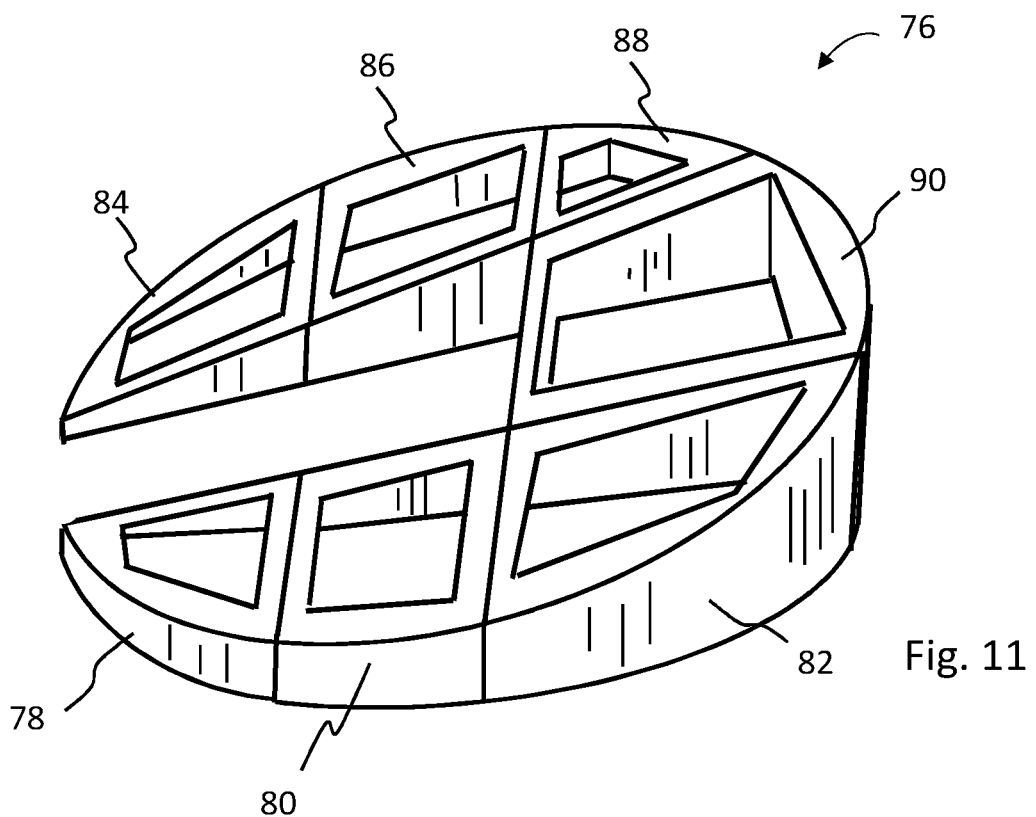
FIG. 11 shows a side perspective view of an embodiment of a generally U-shaped implant for use in a surgical repair of the knee.

FIG. 11 shows another embodiment of a generally U-shaped implant 76 which may be constructed from a plurality of implant subunits. For example, seven separate implant subunits may be used to construct U-shaped implant 76, including lateral anterior implant subunit 78, central anterior implant subunit 80, and medial anterior implant subunit 82. In addition, U-shaped implant 76 may include lateral posterior implant subunit 84, central posterior implant subunit 86, medial posterior implant subunit 88, and medial interior implant subunit 90. As illustrated in the embodiment of U-shaped implant 76, implant subunits may include one or more walls defining an overall shape of an implant subunit. The implant subunits may further include one or more internal cavities. In some embodiments, one or more internal walls or supports may further be included in an implant subunit. Other suitable numbers and arrangements of implant subunits may be included in a wedge-shaped implant. For example, a generally U-shaped implant may have between about 3 implant subunits to about 16 implant subunits or another suitable number and arrangement of subunits may be used.

Figure 12:
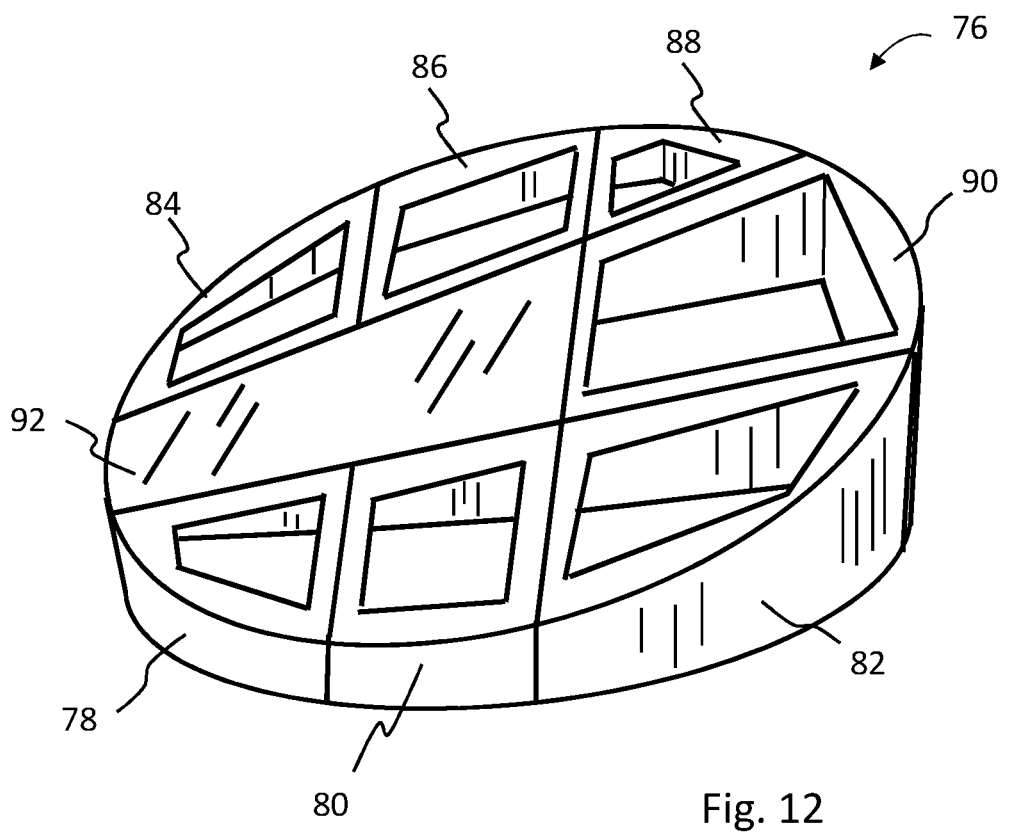
FIG. 12 shows a side perspective view of an embodiment of an implant for use in a surgical repair of the knee.
Figure 12A:
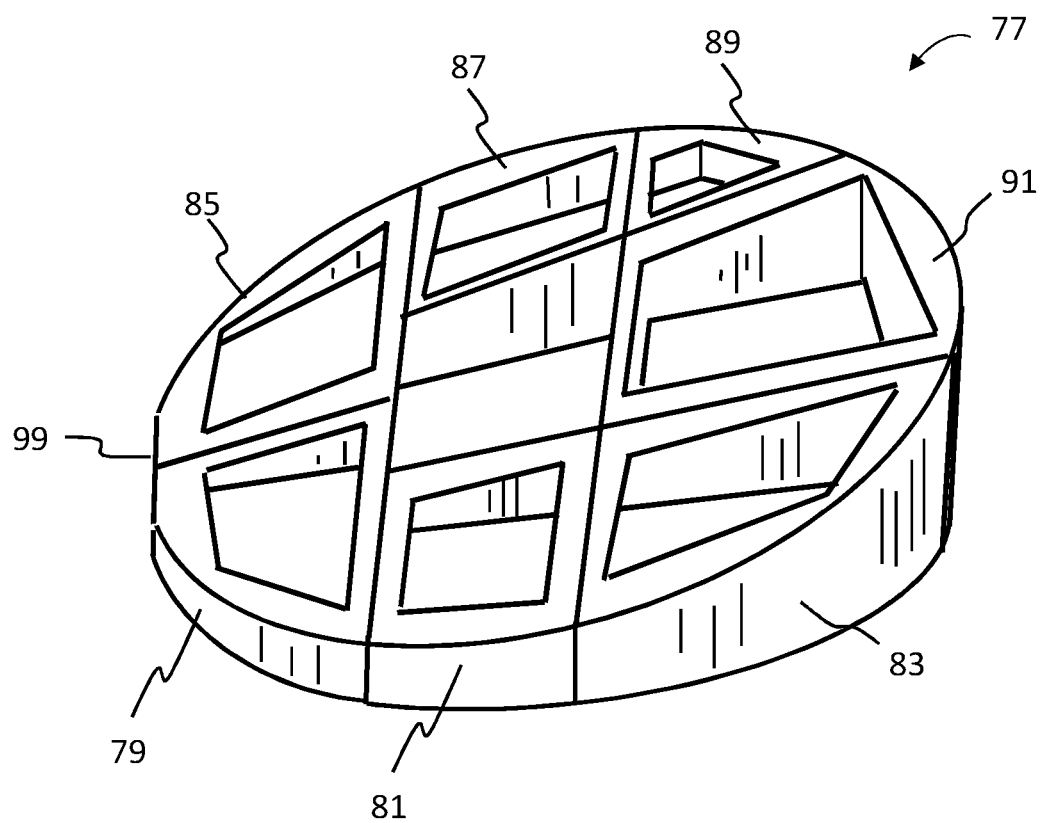
FIG. 12A shows a side perspective view of an embodiment of a ring-shaped implant for use in a surgical repair of the knee.

In some embodiments, a space between individual subunits may be filled with a filling material, such as a matrix material of bony fragments or other material to encourage osteogenesis, for example. In some embodiments, as shown in FIG. 12, a space between implant subunits (78, 80, 82, 84, 86, 88, and 90) may be filled with one or more secondary implant subunits 92. Thus, generally U-shaped implant 76 may, in some embodiments, function as a U-shaped portion of an implant. The implant subunit 92, which may not be in contact with hard cortical bone of rim 44, may be under reduced stress as compared to other implant subunits (e.g., (78, 80, 82, 84, 86, 88, and 90) positioned adjacent rim 44 of cortical bone. In some embodiments, the implant subunit 92 may be made of a material such as a biocompatible plastic or metal that is less expensive than implant subunits (78, 80, 82, 84, 86, 88, and 90). Or, a material for implant subunit 92 may be selected based on other desired characteristics, such as an ability to promote osteogenesis, healing, or to help minimize a risk of infection. FIG. 12A shows an additional embodiment of a ring-shaped implant 77. Ring-shaped implant 77 may include subunits (79, 81, 83, 85, 87, 89, and 91). In some embodiments, ring-shaped implant 77 may be used to provide substantially continuous and complete coverage of cortical bone of rim 44, including, for example, near implant side 99 which may, for example, abut against hinge portion 48, if present.

Figure 13:
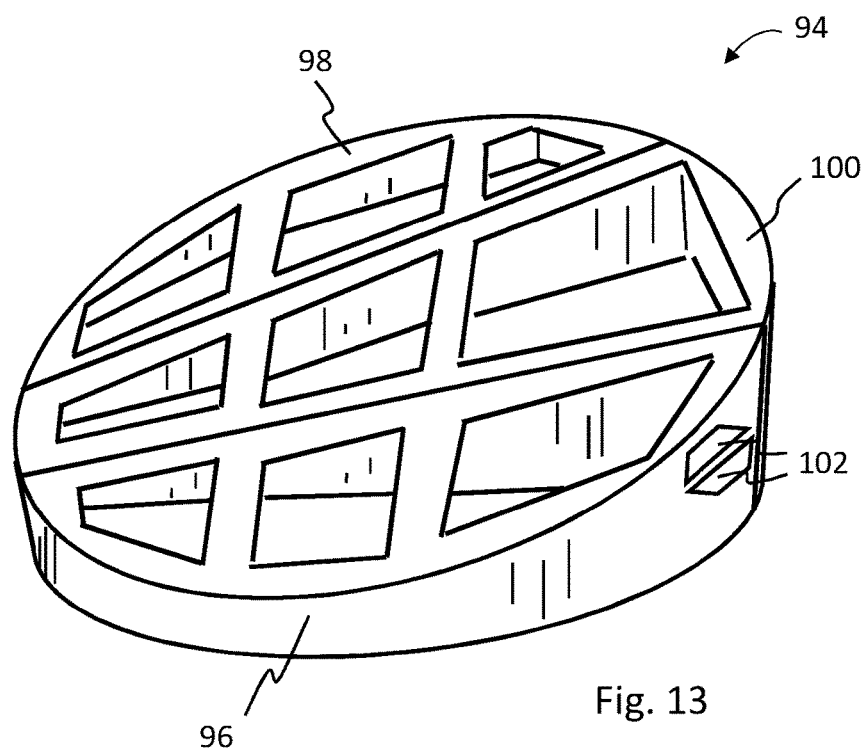
FIG. 13 shows a side perspective view of another embodiment of an implant for use in a surgical repair of the knee.
Figure 14:
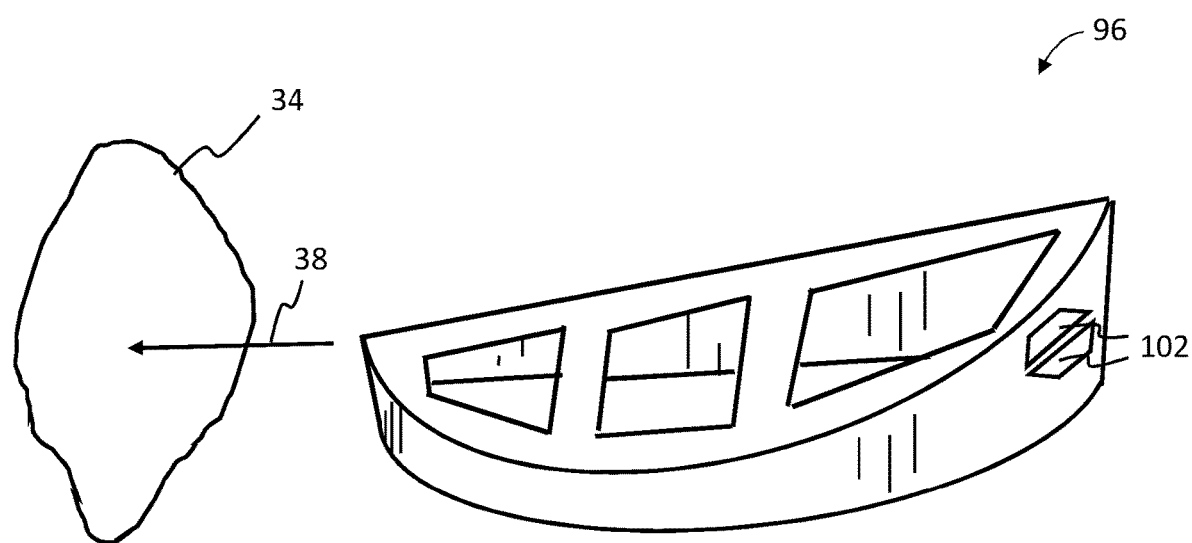
FIG. 14 shows an implant subunit and positioning of the subunit during a part of a surgical repair of the knee.

FIG. 13 shows an additional embodiment of an implant 94. Implant 94 may comprise three implant subunits, including anterior implant subunit 96, posterior implant subunit 98, and interior implant subunit 100. Notably, the implant subunits 96, 98, and 100 may include a substantially longer length than a width. A surgeon may choose to insert the implant subunits 96, 98, and 100 through an opening 34 and within a wedge-shaped void 10 of the tibia 12 in an orientation to minimize a cross-sectional area subtended by the implant subunits 96, 98, and 100 during insertion and/or to minimize a need for repositioning following insertion. In some embodiments, one or more of the implant subunits 96, 98, and 100 may include one or more features suitable for grasping by a surgeon to facilitate insertion in a specific orientation. For example, one or more of the implant subunits 96, 98, and 100 may include one or more holes, notches, indents, or handles suitably configured so that a surgeon may grasp an implant subunit 96, 98, and 100 with a pair of graspers or other surgical instruments. For example, FIG. 14 shows anterior implant subunit 96 separated from the other implant subunits 98, 100. In some embodiments of a method for insertion of generally U-shaped implant 94, a surgeon may insert the subunit (as shown by insertion arrow 38) through the opening 34 about as oriented in FIG. 14, such that an area subtended by the implant subunit 96 is generally minimized so as to fit through opening 34. To facilitate insertion, implant subunit 96 may include a pair of indents 102 positioned towards a medial end of implant subunit 96 that are configured to be grasped by graspers or another surgical instrument, for example.

Figure 15:
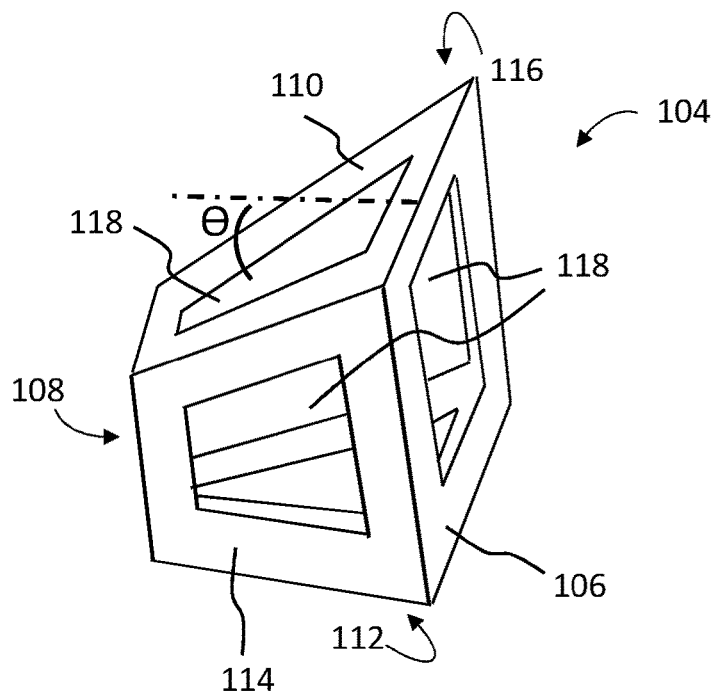
FIG. 15 is a side perspective view of a first embodiment of an implant subunit.

FIG. 15 shows an embodiment of an implant subunit 104. Implant subunit 104 may comprise medial endwall 106, lateral endwall 108, top wall 110, bottom wall 112, first sidewall 114, and second sidewall 116. The walls (e.g., 106, 108, 110, 112, 114, and 116) of implant subunit 104 may be shaped in the form of a square, rectangle, rhombus, parallelogram, trapezoid or other suitable geometric shape. For example, medial endwall 106 and medial endwall 108 may be shaped as rectangles. In some embodiments, one or more of top wall 110 or bottom wall 112 may be oriented at an angle θ relative to a normal vector (shown as a dot-dash line in FIG. 15) of an adjacent endwall 106 or 108. For example, an angle θ may be suitable so that when implant subunit 104 is positioned within wedge-shaped void 10, the walls 110, 112 may follow a taper generally matched to wedge-shaped void 10. For example, in some embodiments, the angle θ may vary from about 7 degrees to about 15 degrees. Similarly, one or more of first sidewall 114 and second sidewall 116 may be oriented at an angle relative to a normal vector of an adjacent endwall 106 or 108. Accordingly, one or more of the sidewalls 114, 116 may be oriented to generally form a generally U-shaped implant including implant subunit 104 in an inward taper.

As shown in FIG. 15, one or more of the walls (106, 108, 110, 112, 114, and 116) of implant subunit 104 may include an opening 118. For example, implant subunit 104 may, at least in part, be hollow. In some embodiments, implant subunit 104 may be porous. Remaining portions of a hollow or porous implant subunit 104 may be configured to bear structural loads from a patient's weight that may be transmitted through the tibia. For example, remaining portions of a hollow or porous implant subunit 104 may comprise a cage suitably configured to bear structural loads from a patient's weight that are transmitted through the tibia. The remaining portions of subunit 104 may comprise a scaffold configured at a density and material composition suitable to withstand forces associated with a patient's weight when used with other implant subunits in an implant. For example, a substantially hollow implant subunit 104 may be used with other substantially hollow implants to form an implant or portion of an implant that may be positioned over at least an exposed rim of cortical bone of a patient's tibia when inserted into a wedge-shaped void of the patient's tibia. A scaffold of sufficient density and suitable material composition (e.g., carbon-fiber or carbon-fiber reinforced PEEK) may be used to support even obese patients who may weigh upwards to about 300 pounds to about 500 pounds, for example. In some embodiments, implants described herein may be filled with one or more biocompatible materials. And, in some embodiments, implants described herein may transfer a portion of a weight of a patient to one or more materials filled within an otherwise hollow portion of implant subunit 104. For example, an otherwise hollow implant subunit 104 may be filled with one or more materials suitable to promote processes including osteogenesis, osteoinduction, osteoconduction, and any combination thereof. For example, hollow portions of an implant subunit may be filled with demineralized bone matrix, hydroxyapatite, one or more growth factors, other suitable matrix materials, and any combination thereof. By way of nonlimiting example, growth factors suitable for use herein may include Transforming Growth Factor "TGF-B," Platelet-Derived Growth Factor "PDGF," Bone-Morphogenic Protein "BMP," and any combination thereof.

Implant subunits described herein may be made from or may include any suitable biologically compatible material or combination of materials. For example, suitable materials may be selected based on one or more of the following characteristics, or other characteristics, including strength, stiffness, biocompatibility, elasticity, and combinations thereof. By way of nonlimiting example, suitable materials for use in implant subunits described herein may include titanium, stainless steel, tantalum, suitable plastics, ceramics, metallic alloys including one or more biologically compatible metals, biocompatible polymers (e.g., polyethylketone (PEEK)), carbon-fiber, carbon-fiber reinforced PEEK, and combinations thereof. In some embodiments, implant subunits may be made from, comprise, or consist of carbon-fiber or carbon-fiber reinforced PEEK.

Figure 16:
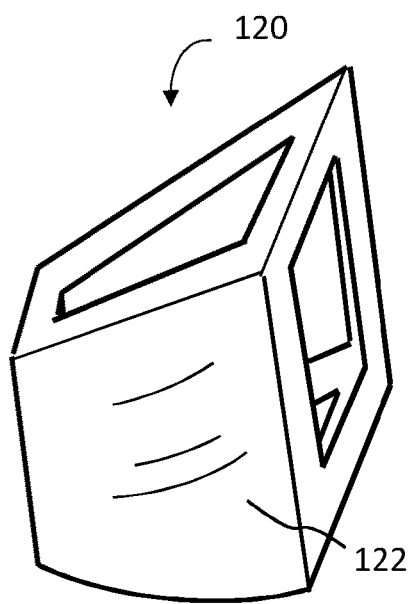
FIG. 16 is a side perspective view of a second embodiment of an implant subunit.
Figure 17:
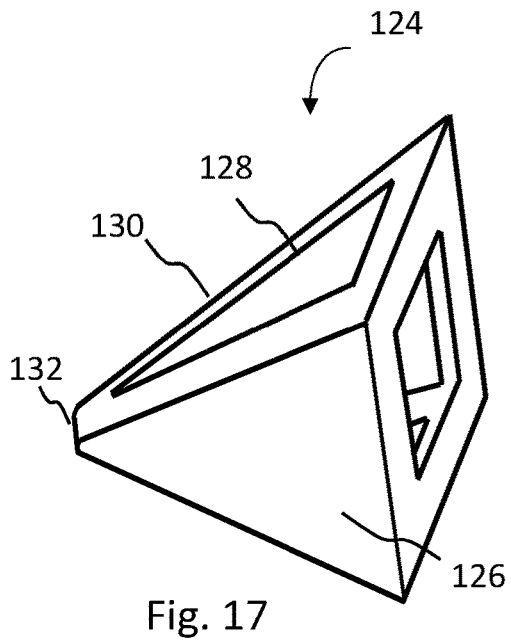
FIG. 17 is a side perspective view of a third embodiment of an implant subunit.

Additional embodiments of implant subunits are also shown in FIGS. 16-20. As shown in FIG. 16, an implant subunit 120 may include one or more curved or shaped walls 122. For example, a curved or shaped wall 122 may be configured to substantially match or trace one or more adjacent surfaces of a patient's bone. As shown in FIG. 17, an implant subunit 124 may be shaped to substantially fill an end of a wedge-shaped void 10. Thus, for example, one or more walls, such as sidewall 126 and top wall 128 of an implant subunit 124 may be substantially triangular in shape. In some embodiments, implant subunit 124 may include one or more rounded edges. For example, edge 130 or edge 132 may be rounded. As shown in FIG. 18, an implant subunit 140 may include one or more holes 142 and/or one or more hooks 144. The one or more holes 142 and/or hooks 144 may be configured to receive one or more pins 146 or cables 148. Alternatively, holes 142 may be threaded, and threaded screws may be used instead of pins 146. In some embodiment, holes may include one or more guiding bores or posts to assist a surgeon in threading a pin 146 or screw through a hole. In some embodiments, one or more cables 148 may be pre-threaded (e.g., within one or more holes 142 or through hooks 144) within an implant subunit 140 prior to insertion of implant subunit. In some embodiments, one or more holes 142 and/or hooks 144 may be positioned on an implant subunit so that a surgeon may readily attach a pin 146, cable 148, or screw. For example, hole 142 may be positioned on an edge 143 that may be more centrally located in a generally U-shaped implant.

As shown in FIG. 19, a pin 146 may be inserted into or through two or more implant subunits 150, 152 in order to link the implant subunits 150, 152 together. As shown in FIG. 20, a pin 146 may extend through two or more implant subunits 150, 152 and also into or through a portion of bone 154.

Figure 21:
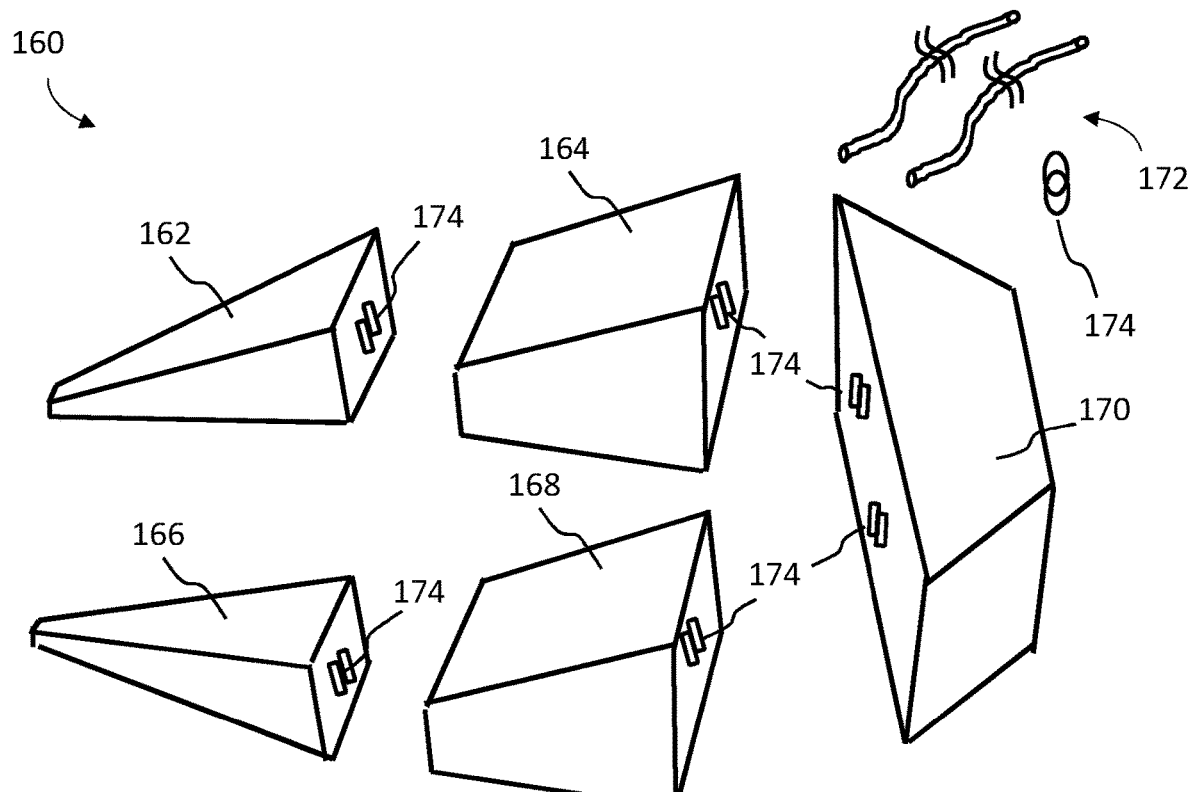
FIG. 21 is a perspective view of a kit for making an implant from a plurality of subunits.
Figure 22:
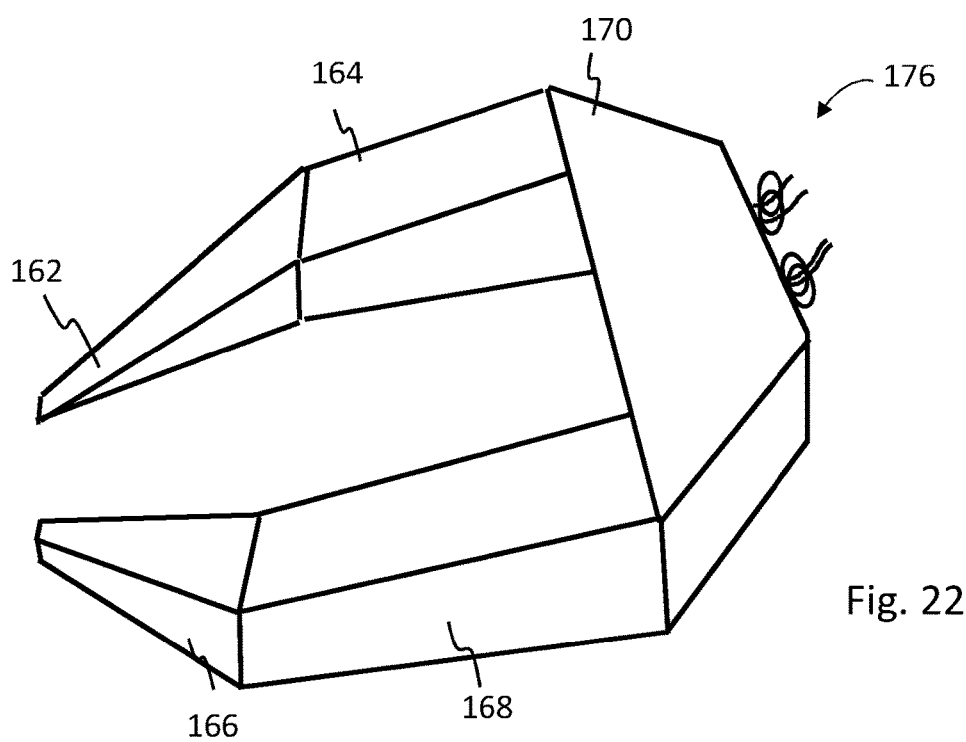
FIG. 22 is a perspective view of a generally U-shaped implant formed by positioning the plurality of subunits shown in FIG. 21.

In some embodiments, kits are described herein which may include one or more components or component types which may be used in a tibial osteotomy and repair. In some embodiments, a kit may include a plurality of implant subunits, the implant subunits configured to form a generally U-shaped implant when the implant subunits are used collectively. The kit may further include one or more linking or stabilizing members configured to physically link the plurality of implant subunits. For example, the kit may include one or more screws, pins, cables, crimping assemblies, wires or combinations thereof as linking members. For example, as shown in FIG. 21, a kit 160 may include an assembly of five implant subunits (162, 164, 166, 168, and 170). Kit 160 may further include a collection of cables 172 and one or more associated crimps 174. For example, cables 172 may be configured for threading through one or more internal holes 174 formed within the implant subunits (162, 164, 166, 168, and 170). A kit may further include instructions for executing one or more of the surgical methods described herein. For example, a kit 160 may include ordered instructions for how to insert, position, and link the plurality of implant subunits (162, 164, 166, 168, and 170) in order to assemble a generally U-shaped implant 176 as shown in FIG. 22. By way of nonlimiting example, instructions may be provided in the form of one or more computer readable media, printed instructions, or combinations thereof.

In some embodiments, an implant may include one or more surfaces configured to substantially match a surface made by cutting and/or removing a section of tibial bone. For example, the specific shape of an implant may be designed using one or more computer models and/or computer modeling techniques. For example, the shape of an implant may be designed using one or more computer aided design (CAD) computer programs. And, in some embodiments, the shape of an implant may be specifically based on a patient's anatomy, such as may be obtained using MRI and/or CT scanning techniques, for example.

Figure 23:
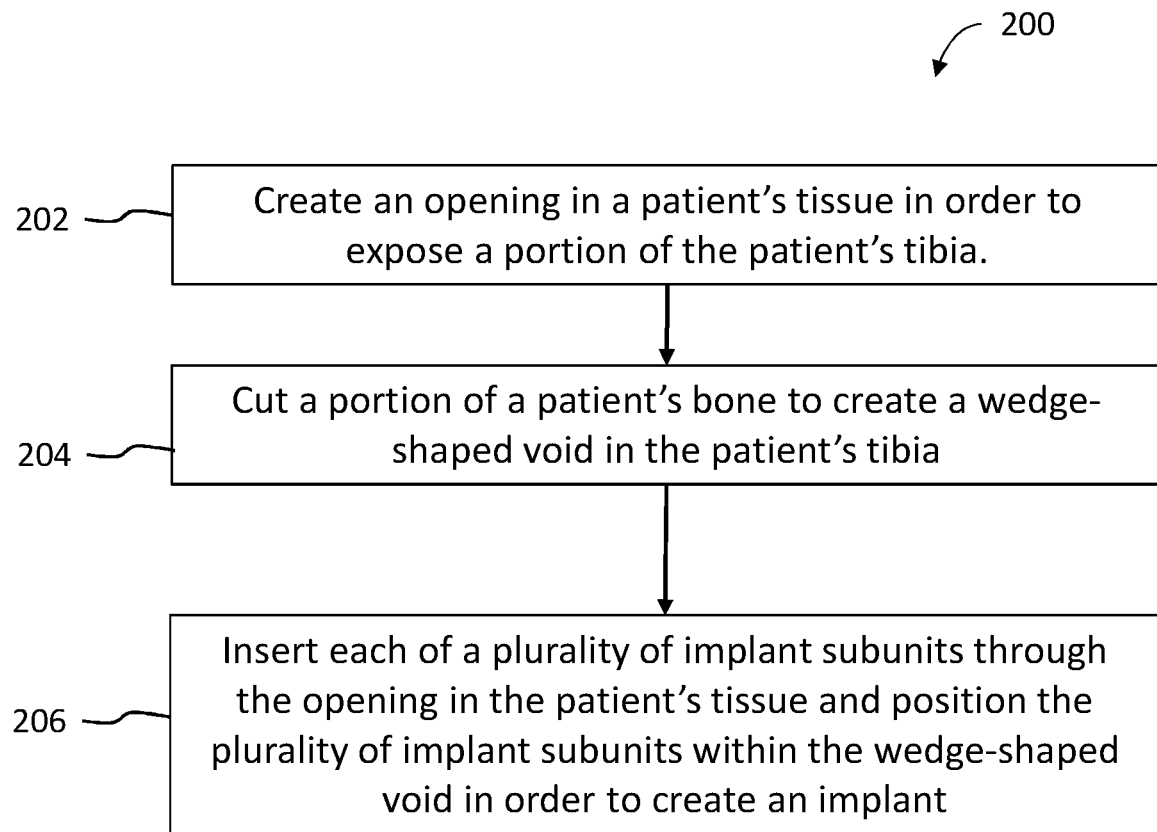
FIG. 23 is a flowchart of a method for inserting an implant into a section of a patient's tibia to perform an opening wedge osteotomy.

FIG. 23 is a flowchart showing an embodiment of a method 200 for inserting an implant in a wedge-shaped void formed by an osteotomy. In step 202, an opening in a patient's tissue may be made, wherein the opening is suitable to expose a portion of the patient's tibia. For example, an opening of limited size, such as a size appropriate for insertion of implant subunits, may be made in the patient's tissue. In some embodiments, the opening may be smaller than necessary for a surgeon to fit a prefabricated U-shaped or wedge-like implant therein. In step 204, a portion of a patient's tibia bone may be cut and opened in order to create a wedge-shaped void in the tibia. Or, a portion of tibia bone may be cut and removed to form a wedge-shaped void in the tibia. In step 206, each of a plurality of implant subunits may be inserted through the opening in the patient's tissue, and the plurality of implant subunits may be positioned within the wedge-shaped void in order to create an implant.

Figure 24:
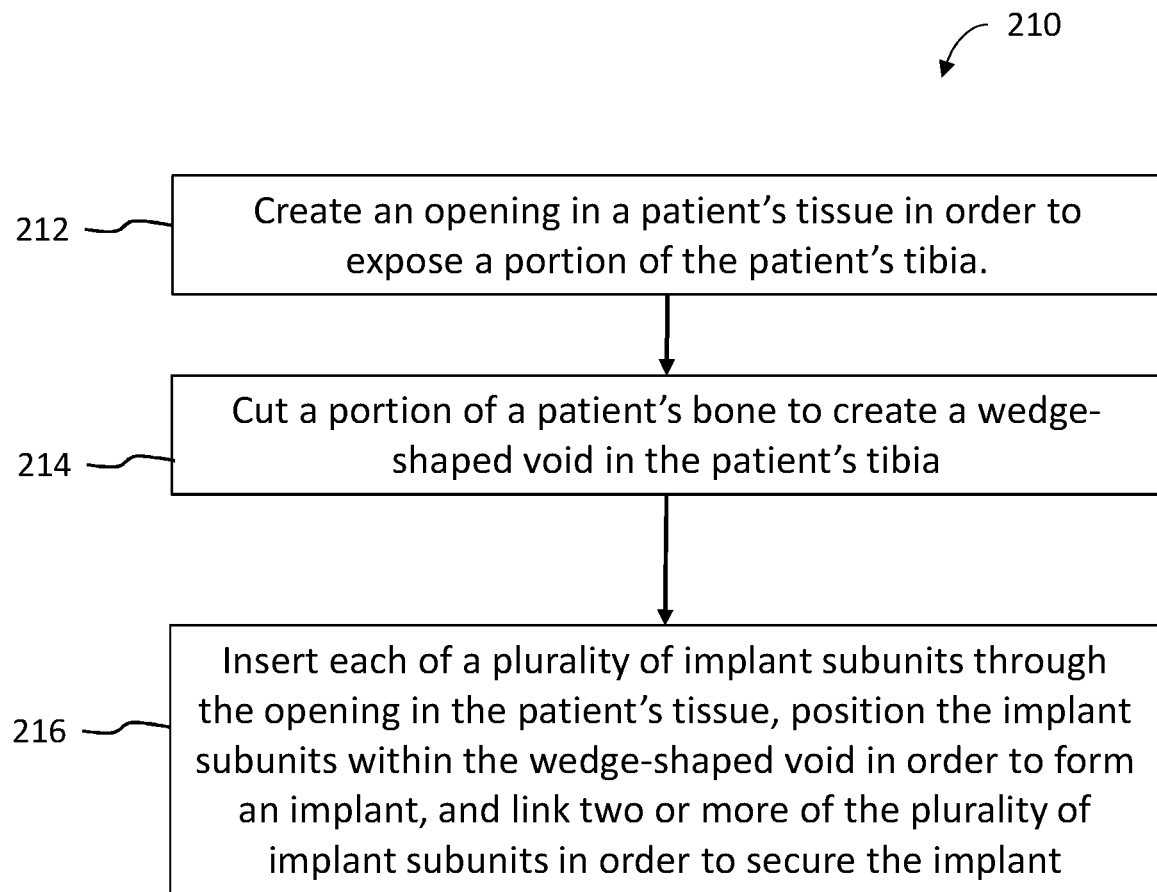
FIG. 24 is a flowchart of another method for inserting an implant into a section of a patient's tibia.

FIG. 24 is a flowchart showing an additional embodiment of a method 210 for inserting an implant in an osteotomy. In step 212, an opening in a patient's tissue may be made, wherein the opening is suitable to expose a portion of the patient's tibia. For example, an opening of limited size, such as a size appropriate for insertion of implant subunits, may be made in the patient's tissue. In some embodiments, the opening may be smaller than necessary for a surgeon to fit a prefabricated U-shaped implant or wedge-like implant therein. In step 214, a portion of a patient's tibia bone may be cut and opened in order to create a wedge-shaped void in the tibia. Or, a portion of tibia bone may be cut and removed to form a wedge-shaped void in the tibia. In step 216, each of a plurality of implant subunits may be inserted within the opening in the patient's tissue, the plurality of implant subunits may be positioned within the wedge-shaped void, and two or more of the individual implant subunits may be linked in order to create an implant.

In some embodiments, positioning of implant subunits in the steps 206, 216 may include attaching, such as by internally threading, one or more cables or wires to one or more implant subunits among a plurality of implant subunits. A surgeon may then pull or tighten the one or more cables or wires in order to automatically position the one or more implant subunits in relation to other subunits in order to assemble an implant. Once positioned, a cable or wire may be crimped or otherwise secured to maintain the desired position and to link the subunits together. Alternatively, the one or more cables or wires may simply be removed. For example, a positioning guide wire may be used to position a plurality of implant subunits in order to assemble an implant. Once the implant subunit is positioned, the guide wire may be removed.

In some embodiments, positioning of implant subunits in the steps 206, 216 may include inserting one or more secondary implant subunits and generally positioning one or more implant subunits along a periphery of the one or more secondary implant subunits. Once generally positioned a surgeon may engage one or more cables to automatically position implant subunits in a position adjacent the one or more secondary implant subunits. To assist in orienting the implant subunits, adjacent implant subunits may include one or more surface features to direct implant surfaces in correct relative alignment.

In some embodiments, positioning of the plurality of implant subunits may include manual manipulation of individual subunits. For example, a surgeon may individually move individual subunits to a desired position, such as along a rim of cortical bone using one or more surgical instruments, such as surgical graspers.

Persons of ordinary skill in the art will understand that implant subunits described herein may be positioned adjacent each other such that a given subunit touches one or more other subunits, or in some embodiments a given subunit may be spaced apart from other subunits. Additionally, whether a given subunit is adjacent or spaced apart with respect to another subunit, the given subunit may or may not be linked to one or more other subunits.

In some embodiments, an implant may be configured for insertion into a wedge-shaped void of a patient's tibia, the implant including a plurality of implant subunits configured to form a generally U-shaped portion of the implant in plan view when the plurality of implant subunits are positioned with respect to each other. The generally U-shaped portion may have a generally wedge-shaped thickness profile. One or more cables may be configured for engaging at least some of the plurality of implant subunits. The one or more cables may be configured such that when the one or more cables are tightened, the plurality of implant subunits may be automatically positioned to stabilize the implant. In some embodiments, one or more implant subunits among the plurality of implant subunits may include a hole configured for receiving of a pin or screw, the pin or screw configured to attach the one or more implant subunits to a portion of a patient's bone. For example, two or more implant subunits among the plurality of implant subunits may include a hole configured for receiving of a pin or screw, the pin or screw configured to link the two or more implant subunits together. The one or more cables may be secured to at least some of the plurality of implant subunits using one or more fastener, hole, hook, or any combination thereof. In some embodiments, the one or more cables may include a first cable configured for engagement with a first group of implant subunits among the plurality of implant subunits and a second cable configured for engagement with a second group of implant subunits among the plurality of implant subunits. Each of the first and second cables may include a free end that protrudes from a medial side of the generally U-shaped portion. One or more of the plurality of implant subunits may be made of carbon-fiber or carbon-fiber reinforced PEEK. One or more of the plurality of implant subunits may include a substantially hollow carbon-cage. In some embodiments, a first member of the plurality of implant subunits may include a first surface that is complementary in shape to a second surface of a second member among the plurality of implant subunits. The first surface and the second surface may be configured to automatically orient the first member and the second member in an orientation suitable for forming the generally U-shaped portion of an implant when the one or more cables are tightened. The implant may include one or more secondary implant subunits. The one or more secondary implant subunits may be made of a material including, for example, titanium, stainless steel, tantalum, plastic, ceramic, metal alloy, biologically compatible metal, biocompatible polymer, and any combination thereof.

In some embodiments, a kit for performing a surgical tibia repair may include a plurality of implant subunits. The plurality of implant subunits may be configured for arrangement with respect to one another to form a generally U-shaped portion of an implant in plan view, the generally U-shaped portion having a generally wedge-shaped thickness profile. The kit may further include one or more linking members and instructions for how to assemble the plurality of implant subunits into the implant using the one or more linking members. One or more of the plurality of implant subunits may be made of carbon-fiber or carbon-fiber reinforced PEEK. The plurality of implant subunits may include a substantially hollow carbon-cage.

In some embodiments, a kit for performing a surgical tibia repair may include a plurality of implant subunits. The plurality of implant subunits may be configured for arrangement with respect to one another to form an implant shaped to substantially cover an exposed rim of cortical bone adjacent a wedge-shaped void in a patient's tibia. The kit may also include one or more linking members and instructions for how to connect the plurality of implant subunits to the one or more linking members and how to automatically position the implant subunits to form the implant when tightening the one or more linking members. The plurality of implant subunits may include a plurality of implant subunits configured for bearing a patient's weight. The plurality of implant subunits for bearing the patient's weight may include a substantially hollow carbon-cage. In some embodiments, the plurality of implant subunits may include one or more secondary implant subunits. The one or more secondary implant subunits may be configured for positioning over an exposed region of trabecular bone adjacent the wedge-shaped void. The one or more secondary implant subunits may be sized and shaped for positioning over an exposed region of trabecular bone adjacent a wedge-shaped void. The one or more secondary implant subunits may assist in positioning a generally U-shaped portion of the plurality of implant subunits over the exposed rim of cortical bone when tightening the one or more linking members. The one or more secondary implant subunits may be sized and angled for positioning over an exposed region of trabecular bone adjacent the wedge-shaped void. At least one of the one or more secondary implant subunits may include at least one surface that is complementary in shape to at least one other surface included in at least one of the plurality of implant subunits.

In some embodiments, a method of installing an orthopedic implant may include creating an opening in a patient's tissue in order to expose a portion of the patient's tibia and cutting a portion of the patient's tibia to create a wedge-shaped void therein. The method may further include individually inserting each of a plurality of implant subunits through the opening in the patient's tissue and positioning the plurality of implant subunits within the wedge-shaped void to form a generally U-shaped portion of the implant. In some embodiments, positioning the plurality of implant subunits may include generally positioning the plurality of implant subunits on an exposed surface of the patient's tibia adjacent the wedge-shaped void, securing one or more cables to at least some of the plurality of implant subunits, and tightening the one or more cables to automatically direct the plurality of implant subunits to form the generally U-shaped portion. The generally U-shaped portion may substantially overlap an exposed rim of cortical bone of the exposed surface of the patient's tibia. Two or more of the plurality of implant subunits may further be linked. In some embodiments, the plurality of implant subunits may include one or more secondary implant subunits and a plurality of other implant subunits. In those embodiments, positioning the plurality of implant subunits may include generally positioning the plurality of implant subunits on an exposed surface of the patient's tibia adjacent the wedge-shaped void. For example, the one or more secondary implants may be generally positioned over a trabecular portion of the exposed surface. The plurality of other implant subunits may further be generally positioned along a periphery of the one or more secondary implant subunits. Positioning the plurality of implant subunits may then include securing one or more cables to the plurality of other implant subunits and tightening the one or more cables to automatically direct the plurality of other subunits to abut against at least one of the one or more secondary implant subunits to form the generally U-shaped portion. The generally U-shaped portion may substantially overlap an exposed rim of cortical bone of the exposed surface of the patient's tibia. For example, the generally U-shaped portion may overlap an area that is greater than about 75% of an area of the exposed rim of cortical bone.

In some embodiments, an implant may be configured for insertion into a wedge-shaped void of a patient's tibia. The implant may include a plurality of implant subunits, the plurality of implant subunits configured to shape the implant to substantially fill the wedge-shaped void when the plurality of implant subunits are positioned with respect to each other. One or more of the plurality of implant subunits may include a substantially hollow carbon-cage made of carbon-fiber or carbon-fiber reinforced PEEK. The implant may have a generally wedge-shaped thickness profile. The implant may, for example, be selected from a generally U-shaped implant and a ring-shaped implant. In some embodiments, the implant may further include one or more cables configured for engaging at least some of the plurality of implant subunits. The one or more cables may be configured such that when the one or more cables are tightened, the plurality of implant subunits is automatically positioned to form the implant. In some embodiments, the implant may further include one or more cables and one or more pins or screws. The one or more cables may be configured for engaging at least some of the plurality of implant subunits, the one or more cables configured such that when the one or more cables are tightened the plurality of implant subunits is automatically stabilized. Each of one or more implant subunits among the plurality of implant subunits may include a hole configured for receiving at least one screw or pin among the one or more pins or screws. The one or more pins or screws may further be configured to attach the one or more implant subunits to a portion of the patient's bone. In some embodiments, two or more implant subunits among the plurality of implant subunits may include a hole configured for receiving of a pin or screw, the pin or screw configured to link the two or more implant subunits together. In some embodiments, the implant may include one or more cables configured for engaging at least some of the plurality of implant subunits, the one or more cables including a first cable configured for engagement with a first group of implant subunits among the plurality of implant subunits and a second cable configured for engagement with a second group of implant subunits among the plurality of implant subunits. Each of the first cable and the second cable may include a free end that protrudes from a medial side of the implant. In some embodiments, the implant may include one or more cables configured for engaging at least some of the plurality of implant subunits, a first member of the plurality of implant subunits including a first surface that is complementary in shape to a second surface of a second member among the plurality of implant subunits. The first surface and the second surface may be configured to automatically orient the first member and the second member in an orientation suitable for forming the implant when the one or more cables are tightened. In some embodiments, the implant may include a first group of implant subunits and a second group of implant subunits. The first group of implant subunits being the one or more of said plurality of implant subunits that comprise the substantially hollow carbon-cage made of carbon-fiber or carbon-fiber reinforced PEEK, the first group of implant subunits shaped to be positioned over an exposed rim of cortical bone of a patient's tibia when inserted into said wedge-shaped void of the patient's tibia. The second group of implant subunits being one or more secondary implant subunits sized and shaped for positioning over an exposed region of trabecular bone of a patient's tibia when inserted into the wedge-shaped void of the patient's tibia. The one or more secondary implant subunits may be made of or include a material selected from titanium, stainless steel, tantalum, plastic, ceramic, metal alloy, biologically compatible metal, biocompatible polymer, and any combination thereof.

Although the methods, kits, and apparatus disclosed herein and some of their advantages have been described in detail, it should be understood that various changes, substitutions and alterations may be made herein without departing from the invention as defined by the appended claims and their legal equivalents. For example, among other things, any feature described for one embodiment may be used in any other embodiment, and any feature described herein may be used independently or in combination with other features. Moreover, the scope of the present application is not intended to be limited to the particular embodiments of the apparatuses, kits, methods and steps described in the specification. Use of the word "include," for example, should be interpreted as the word "comprising" would be, i.e., as open-ended. As one will readily appreciate from the disclosure, processes, machines, manufactures, compositions of matter, means, methods, or steps presently existing or later to be developed that perform substantially the same function or achieve substantially the same result as the corresponding embodiments described herein may be utilized. Accordingly, the appended claims are intended to include within their scope such processes, machines, manufactures, compositions of matter, means, methods or steps.

What is claimed is:

1. A kit for performing a surgical tibia repair, the kit comprising:
 a plurality of implant subunits;
 wherein said plurality of implant subunits are configured for arrangement with respect to one another to form an implant shaped to substantially cover an exposed rim of cortical bone adjacent a wedge-shaped void in a patient's tibia;
 one or more linking members; and
 instructions for how to connect said plurality of implant subunits to said one or more linking members and how to automatically position said implant subunits to form said implant when tightening said one or more linking members;

wherein said plurality of implant subunits include a plurality of implant subunits configured for bearing a patient's weight, said plurality of implant subunits comprising a substantially hollow carbon-cage.

2. The kit of claim 1 wherein said plurality of implant subunits include one or more secondary implant subunits.

3. The kit of claim 2 wherein said one or more secondary implant subunits are configured for positioning over an exposed region of trabecular bone adjacent the wedge-shaped void.

4. The kit of claim 2 wherein said one or more secondary implant subunits are sized and shaped for positioning over an exposed region of trabecular bone adjacent said wedge-shaped void;

wherein said one or more secondary implant subunits assist in positioning a generally U-shaped portion of said plurality of implant subunits over said exposed rim of cortical bone when tightening said one or more linking members.

5. The kit of claim 2 wherein said one or more secondary implant subunits are sized and angled for positioning over an exposed region of trabecular bone adjacent said wedge-shaped void;

wherein at least one of said one or more secondary implant subunits includes at least one surface that is complementary in shape to at least one other surface included in at least one of said plurality of implant subunits.

* * * * *